(12) United States Patent
Cary

(10) Patent No.: US 9,120,715 B2
(45) Date of Patent: *Sep. 1, 2015

(54) ALKYLATION OF AROMATIC SUBSTRATES

(71) Applicant: TOTAL PETROCHEMICALS FRANCE, Paris (FR)

(72) Inventor: Jean-Bernard Cary, Le Havre (FR)

(73) Assignee: TOTAL PETROCHEMICALS FRANCE, Puteaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/224,973

(22) Filed: Mar. 25, 2014

(65) Prior Publication Data

US 2014/0206917 A1 Jul. 24, 2014

Related U.S. Application Data

(63) Continuation of application No. 14/098,088, filed on Dec. 5, 2013, now Pat. No. 8,742,191, which is a continuation of application No. 12/937,581, filed as application No. PCT/EP2009/053992 on Apr. 3, 2009, now Pat. No. 8,802,910.

(30) Foreign Application Priority Data

Apr. 18, 2008 (EP) ..................................... 08290392

(51) Int. Cl.
| | |
|---|---|
| *C07C 2/66* | (2006.01) |
| *C07C 2/64* | (2006.01) |
| *C07C 6/12* | (2006.01) |
| *C07C 6/06* | (2006.01) |

(52) U.S. Cl.
CPC ... *C07C 2/64* (2013.01); *C07C 2/66* (2013.01); *C07C 6/06* (2013.01); *C07C 6/126* (2013.01)

(58) Field of Classification Search
USPC .................................................. 585/448, 467
See application file for complete search history.

(56) References Cited

U.S. PATENT DOCUMENTS

| | | | |
|---|---|---|---|
| 3,751,504 A | 8/1973 | Keown et al. | |
| 4,016,218 A | 4/1977 | Haag et al. | |
| 4,169,111 A | 9/1979 | Wight | |
| 4,459,426 A | 7/1984 | Inwood et al. | |
| 4,547,605 A | 10/1985 | Kresge et al. | |
| 4,849,569 A | 7/1989 | Smith | |
| 4,891,458 A | 1/1990 | Innes et al. | |
| 4,950,834 A | 8/1990 | Arganbright et al. | |
| 4,954,325 A | 9/1990 | Rubin et al. | |
| 4,992,606 A | 2/1991 | Kushnerick et al. | |
| 5,021,141 A | 6/1991 | Rubin | |
| 5,030,786 A | 7/1991 | Shamshoum et al. | |
| 5,077,445 A | 12/1991 | Le | |
| 5,081,323 A | 1/1992 | Innes et al. | |
| 5,086,193 A | 2/1992 | Sy | |
| 5,113,031 A | 5/1992 | Sy | |
| 5,157,185 A | 10/1992 | Chu et al. | |
| 5,160,497 A | 11/1992 | Juguin et al. | |
| 5,198,595 A | 3/1993 | Lee et al. | |
| 5,215,725 A | 6/1993 | Sy | |
| 5,236,575 A | 8/1993 | Bennett et al. | |
| 5,240,889 A | 8/1993 | West et al. | |
| 5,250,277 A | 10/1993 | Kresge et al. | |
| 5,258,565 A | 11/1993 | Kresge et al. | |
| 5,292,698 A | 3/1994 | Chu et al. | |
| 5,334,795 A | 8/1994 | Le | |
| 5,362,697 A | 11/1994 | Fung et al. | |
| 5,371,310 A | 12/1994 | Bennett et al. | |
| 5,430,211 A | 7/1995 | Pogue et al. | |
| 5,437,855 A | 8/1995 | Valyocsik | |
| 5,453,554 A | 9/1995 | Cheng et al. | |
| 5,493,065 A | 2/1996 | Cheng et al. | |
| 5,522,984 A | 6/1996 | Gajda et al. | |
| 5,536,894 A | 7/1996 | Degnan et al. | |
| 5,557,024 A | 9/1996 | Cheng et al. | |
| 5,563,311 A | 10/1996 | Chang et al. | |
| 5,569,805 A | 10/1996 | Beck et al. | |

(Continued)

FOREIGN PATENT DOCUMENTS

| | | | |
|---|---|---|---|
| EP | 0467007 A1 | 1/1992 | |
| EP | 0485683 A1 | 5/1992 | |
| EP | 0507761 A1 | 10/1992 | |
| EP | 0726242 A1 | 8/1996 | |
| EP | 0733608 A1 | 9/1996 | |
| EP | 0826653 A1 | 3/1998 | |
| EP | 0844023 A2 | 5/1998 | |
| EP | 0879809 A1 | 11/1998 | |
| EP | 0943594 A1 | 9/1999 | |
| EP | 1002778 A1 | 5/2000 | |

(Continued)

OTHER PUBLICATIONS

Office Action and Search Report issued in Chinese Application No. 200980123312.9 mailed on Jan. 27, 2014, and English translation thereof, 23 pages.

*Primary Examiner* — Thuan D Dang

(57) ABSTRACT

A process for the alkylation of an aromatic substrate can include providing an alkylation reaction zone containing an alkylation catalyst, and introducing a feedstock including an aromatic substrate and an alkylating agent into an inlet of the alkylation reaction zone and into contact with the alkylation catalyst. The alkylation reaction zone can be operated at temperature and pressure conditions to cause alkylation of the aromatic substrate in the presence of the alkylation catalyst to produce an alkylation product including a mixture of the aromatic substrate and monoalkylated and polyalkylated aromatic components. The alkylation product can be withdrawn from the alkylation reaction zone. Nitrogen containing compounds in the aromatic substrate, alkylating agent, or both can be monitored in a range 15 wppb to 35 wppm by dry colorimetry. The process can include transalkylation of polyalkylated aromatic components in a transalkylation reaction zone containing a transalkylation catalyst.

20 Claims, No Drawings

(56) References Cited

U.S. PATENT DOCUMENTS

| | | | |
|---|---|---|---|
| 5,672,799 A | 9/1997 | Perego et al. |
| 5,689,025 A | 11/1997 | Abichandani et al. |
| 5,900,520 A | 5/1999 | Mazzone et al. |
| 5,907,073 A | 5/1999 | Ghosh et al. |
| 5,980,859 A | 11/1999 | Gajda et al. |
| 6,002,057 A | 12/1999 | Hendriksen et al. |
| 6,049,018 A | 4/2000 | Calabro et al. |
| 6,051,521 A | 4/2000 | Cheng et al. |
| 6,060,632 A | 5/2000 | Takamatsu et al. |
| 6,162,416 A | 12/2000 | Gajda et al. |
| 6,268,305 B1 | 7/2001 | Butler et al. |
| 6,617,482 B1 | 9/2003 | Venkat et al. |
| 7,199,275 B2 | 4/2007 | Smith |
| 2005/0143612 A1 | 6/2005 | Hwang et al. |

FOREIGN PATENT DOCUMENTS

| | | | |
|---|---|---|---|
| EP | 1031549 | A1 | 8/2000 |
| EP | 1043296 | A2 | 10/2000 |
| EP | 1059277 | A1 | 12/2000 |
| EP | 1188734 | A1 | 3/2002 |
| EP | 1208907 | A1 | 5/2002 |
| EP | 1211233 | A1 | 6/2002 |
| EP | 1546071 | A2 | 6/2005 |
| EP | 1556318 | A1 | 7/2005 |
| EP | 1581466 | A2 | 10/2005 |
| EP | 1691923 | A1 | 8/2006 |
| EP | 1727860 | A2 | 12/2006 |
| EP | 1807201 | A2 | 7/2007 |
| EP | 1851184 | A2 | 11/2007 |
| WO | 00/35836 | A1 | 6/2000 |
| WO | 2007081923 | A2 | 7/2007 |

ALKYLATION OF AROMATIC SUBSTRATES

CROSS-REFERENCE TO RELATED APPLICATIONS

This application is a Continuation of U.S. application Ser. No. 14/098,088, filed on Dec. 5, 2013, which is a Continuation of U.S. application Ser. No. 12/937,581, filed on Jan. 26, 2011, which claims the benefit of PCT/EP2009/053992, filed on Apr. 3, 2009, which claims priority from EP 08290392.3, filed on Apr. 18, 2008.

FIELD OF THE INVENTION

The present invention relates to the alkylation of aromatic substrates and related transalkylation process. The alkylation of aromatic substrates such as benzene to produce alkylated aromatics such as ethylbenzene and diethylbenzene are known in the art. More precisely the invention relates to the monitoring of the nitrogen containing compounds impurities in the aromatic substrate feedstock and/or in the alkylating agent feedstock. The transalkylation of polyalkylated aromatics such as diethylbenzene with an aromatic substrate such as benzene to produce alkylated aromatics such as ethylbenzene is known in the art. The present invention also relates to the monitoring of the nitrogen containing compounds impurities in the aromatic substrate feedstock of said transalkylation process.

BACKGROUND OF THE INVENTION

Alkylation and transalkylation processes using catalysts are often subject to catalyst regeneration and replacement requirements resulting from poisoning of the catalyst by one or more impurities contained in the hydrocarbon feedstock. In many cases, catalyst developments, e.g. to reduce coke-forming and other by-product reactions, have progressed to the stage where poisoning by feedstock impurities is the primary reason that catalyst performance deteriorates which forces the catalyst to be replaced or regenerated. Aromatics alkylation processes employing molecular sieve catalysts can be conducted in either the vapor phase or the liquid phase. However, in view of the improved selectivity and decreased capital and operating costs associated with liquid phase operation, most commercial alkylation processes now operate under at least partial liquid phase conditions. Unfortunately, one disadvantage of operating under liquid phase conditions is that the molecular sieve catalysts tend to be more sensitive to the presence of impurities in the feedstocks, particularly polar compounds such as nitrogen compounds. Such impurities reduce the acid activity of the catalyst and hence decrease the cycle time between required regenerations of the catalyst. Various processes have been developed for removal of such impurities prior to contact with the catalyst. In the following prior arts there are description of said impurities as well as processes to remove these impurities.

U.S. Pat. No. 6,002,057 describes a process for the alkylation of an aromatic hydrocarbon contained in a hydrocarbon stream comprising:

(a) separating essentially all aromatics other than said aromatic hydrocarbon from said hydrocarbon stream, thereby forming an aromatic-rich stream;
(b) treating said aromatic-rich stream of (a) by converting essentially all olefinic compounds contained therein by hydrogenation;
(c) contacting the thus treated aromatic-rich stream from (b) with an olefin-containing stream comprising at least one olefin selected from the group consisting of ethylene, propylene, and butylene, wherein the molar ratio of the olefin(s) to said aromatic hydrocarbon is not less than 1 in the presence of a catalyst comprising zeolite beta, under alkylation conditions, whereby mono and polyalkylated aromatics are formed; and
(d) separating said mono and polyalkylated aromatics formed in (c) from the remaining hydrocarbons.

At col 6 lines 48-53 is mentioned that the olefins may be present in admixture with hydrogen, methane, C2 to C4 paraffins, but it is usually preferable to remove dienes, acetylenes, sulfur compounds or basic nitrogen compounds (NH3 or amines) which may be present in the olefin feedstock stream, to prevent rapid catalyst deactivation.

U.S. Pat. No. 6,617,482 describes a process for removing polar compounds from an aromatic feedstock which contains polar compounds and which is then used in an alkylation process. The process comprises contacting the feedstock in an adsorption zone at a temperature of less than or equal to 130° C. with an adsorbent selective for the adsorption of said polar compounds and comprising a molecular sieve having pores and/or surface cavities with cross-sectional dimensions greater than 5.6 Angstroms. A treated feedstock substantially free of said polar compounds is withdrawn from the adsorption zone and fed to an alkylation zone for contact under liquid phase alkylation conditions with an alkylating agent in the presence of an alkylation catalyst. More particularly, this prior art relates to a liquid phase aromatics alkylation process which includes subjecting the aromatic feedstock to a pretreatement step for the selective removal of polar contaminants that poison aromatic alkylation catalysts. Such contaminants include nitrogen, sulfur, and oxygen containing compounds, particularly those that boil in the same ranges as benzene, toluene or xylenes.

US 2005 0143612 describes a process for the production of alkyl aromatic compounds wherein aromatic compounds which may be treated for removal of deleterious substances are reacted with olefin compounds, which may also be treated for contaminant removal, in the presence of acidic zeolite catalyst(s) to produce the desired alkyl aromatic compound(s). The aromatic and preferably also the olefin feeds are treated substantially to remove contaminants, particularly the nitrogen compounds contained therein, before they are brought together for reaction in the presence of the zeolite catalyst(s). The feed pretreatment for removal of nitrogen compounds significantly improves the run length and life of the acidic zeolite catalyst(s). A specific object of this prior art is to provide methods and apparatus for treating an olefin or aromatic feedstock for removal of organic or inorganic nitrogen compounds in preparation for a catalytic alkylation or transalkylation process. In accordance with said prior art, it has been found that nitrogen-containing impurities in one or both feedstocks may neutralize the acidic active sites on the acidic zeolite catalyst and thereby reduce catalyst activity and its ability to effect the desired reaction. Long-term accumulation of these nitrogen-containing impurities on the catalyst gradually reduces catalyst activity to the point where plant performance becomes unacceptable, requiring that the plant be shutdown to reactivate, regenerate, or replace the catalyst.

U.S. Pat. No. 7,199,275 relates to a process for alkylation of an aromatic hydrocarbon stream comprising impurities in which said impurities are removed in a pretreatment system having a first stage, a second stage located downstream of said first stage and a cycle length, said process comprising the steps of:

(a) contacting the aromatic hydrocarbon stream with a first molecular sieve which is 13X in said first stage of said pretreatment system, to remove at least a portion of said impurities, to produce a partially treated aromatic hydrocarbon stream;

(b) contacting said partially treated aromatic hydrocarbon stream with a second molecular sieve which is 4A in a second stage of said pretreatment system to remove substantially all of the remaining portion of said impurities, and to produce a fully treated aromatic hydrocarbon stream; and (c) contacting said fully treated aromatic hydrocarbon stream with an alkylating agent in the presence of an alkylation catalyst and under alkylation conditions, to produce an alkylated aromatic hydrocarbon stream; and wherein said cycle length of said pretreatment system is greater than said cycle length using said first stage of said pretreatment system alone or said second stage of said pretreatment system alone.

In a preferred embodiment the process further comprises the step of contacting said alkylating agent of step (c) with a third molecular sieve, to produce a treated alkylating agent, and contacting said treated alkylating agent with said treated aromatic hydrocarbon stream of step (b), to produce said alkylated aromatic hydrocarbon stream of step (c).

However the above prior arts are silent on how to check these impurities in an industrial process. It has now been discovered that by dry colorimetry it was possible to get in less than 5 minutes the amount of the nitrogen containing compounds impurities in the aromatic substrate or in the alkylating agent. A sample of the feedstock to be analyzed is vaporized, unless it is available under gasous phase, and is sent through a porous substrate carrying a reagent which changes color in proportion with the impurities. An electronic device converts the color to the amount of impurities. To improve the response in time, many such apparatus can be used in parallel and a measurement is launched e.g. every minute or every ten seconds. Should the impurities are found to be higher than a requested level the reactor containing the catalyst can be temporarily by-passed.

BRIEF SUMMARY OF THE INVENTION

The present invention is a process for the alkylation of an aromatic substrate comprising:

(a) providing an alkylation reaction zone containing an alkylation catalyst;

(b) introducing a feedstock comprising an aromatic substrate and an alkylating agent into the inlet of said alkylation reaction zone and into contact with said alkylation catalyst;

(c) operating said alkylation reaction zone at temperature and pressure conditions to cause alkylation of said aromatic substrate in the presence of said alkylation catalyst to produce an alkylation product comprising a mixture of said aromatic substrate and monoalkylated and polyalkylated aromatic components;

(d) withdrawing the alkylation product from said alkylation reaction zone;

wherein the nitrogen containing compounds impurities in the aromatic substrate or in the alkylating agent or both in the aromatic substrate and in the alkylating agent are monitored in a range 15 wppb-35 wppm by dry colorimetry.

In an advantageous embodiment the alkylation reaction zone is operated in the liquid phase.

In another embodiment the aromatic substrate is benzene and the alkylating agent is ethylene.

The present invention also relates to a process for the transalkylation of polyalkylated aromatic components comprising:

(a) providing a transalkylation reaction zone containing a transalkylation catalyst;

(b) introducing a feedstock comprising at least a polyalkylated aromatic component deriving from an aromatic substrate into the inlet of said transalkylation reaction zone and into contact with said transalkylation catalyst;

(c) supplying an aromatic substrate to said transalkylation zone, said aromatic substrate being the same as the one of step (b);

(d) operating said transalkylation zone at temperature and pressure conditions to cause disproportionation of said polyalkylated aromatic components to produce a disproportionation product having a reduced polyalkylated aromatic content and an enhanced monoalkylated aromatic content;

(e) withdrawing the disproportionation product from said transalkylation zone;

wherein the nitrogen containing compounds impurities in the aromatic substrate are monitored in a range 15 wppb-35 wppm by dry colorimetry.

In an advantageous embodiment the aromatic substrate is benzene and the polyalkylated aromatic component is diethylbenzene.

DETAILED DESCRIPTION OF THE INVENTION

As regards the catalysts that can be used for alkylation of benzene with propylene and also for transalkylation of benzene and polyisopropylbenzenes in liquid phase include zeolite beta, zeolite Y, zeolite omega, ZSM-5, ZSM-12, ITQ-1, ITQ-2, ERB-3, SSZ-25, MCM-22, MCM-36, MCM-49, MCM-56, MCM-58, MCM-68, faujasite, mordenite, porous crystalline magnesium silicates, and tungstate modified zirconia, all of which are known in the art.

Catalysts that can be used for alkylation of benzene with ethylene and transalkylation of benzene and polyethylbenzenes in liquid phase processes include zeolite beta, zeolite Y, zeolite omega, ZSM-5, ZSM-12, ITQ-1, ITQ-2, ERB-3, SSZ-25, MCM-22, MCM-36, MCM-49, MCM-56, MCM-58, MCM-68, faujasite, mordenite, porous crystalline magnesium silicates, and tungstate modified zirconia.

Most of these catalysts are described in the following patents: WO 2007/081923, EP 0485683, EP 0467007, EP 0507761, EP 1 691 923, EP 0 826 653, EP 0 733 608, EP 0 726 242, EP 0 844 023, EP 0 879 809, EP 943594, EP 1043296, EP 1059277, EP 1002778, EP 1031549, U.S. Pat. No. 6,268, 305, EP 1188734, EP 1211233, EP 1208907, EP 1556318, EP 1546071, EP 1727860, EP 1581466, EP 1807201, EP1851184, the content of each is incorporated by reference in the present application.

MCM-22 and its use to catalyze the synthesis of alkyl aromatics are described, for example, in U.S. Pat. No. 4,954, 325 (Rubin), U.S. Pat. No. 4,992,606 (Kushnerick), U.S. Pat. No. 5,077,445 (Le), U.S. Pat. No. 5,334,795 (Chu), and U.S. Pat. No. 5,900,520 (Mazzone), each of which is incorporated herein by reference. MCM-36 and its use in the synthesis of alkyl aromatics are described in U.S. Pat. No. 5,250,277 (Kresge), U.S. Pat. No. 5,292,698 (Chu), and U.S. Pat. No. 5,258,565 (Kresge), each of which is incorporated herein by reference. MCM-49 and its use in the synthesis of alkyl aromatics are described in U.S. Pat. No. 5,236,575 (Bennett), U.S. Pat. No. 5,493,065 (Cheng) and U.S. Pat. No. 5,371,310 (Bennett), each of which is incorporated herein by reference.

MCM-56 and its use to catalyze the synthesis of alkyl aromatics are described in U.S. Pat. No. 5,362,697 (Fung), U.S. Pat. No. 5,453,554 (Cheng), U.S. Pat. No. 5,536,894 (Degnan), U.S. Pat. No. 5,557,024 (Cheng), and U.S. Pat. No. 6,051,521 (Cheng), each of which is incorporated herein by reference. MCM-58 and its use for the production of alkyl aromatics are described in U.S. Pat. No. 5,437,855 (Valyocsik) and U.S. Pat. No. 5,569, 805 (Beck), each of which is incorporated herein by reference. MCM-68 and its use for the production of alkyl aromatics are described in U.S. Pat. No. 6,049,018 (Calabro), which is incorporated herein by reference.

The use of tungstate modified zirconia to catalyze the synthesis of alkyl aromatics is described in U.S. Pat. No. 5,563,311 (Chang), which is incorporated herein by reference. U.S. Pat. No. 5,081, 323 (Innes), which is incorporated herein by reference, teaches a liquid phase alkylation or transalkylation process using zeolite beta. Production of cumene over zeolite Y is described in U.S. Pat. No. 5,160, 497 (Juguin) and U.S. Pat. No. 5,240,889 (West), which are incorporated herein by reference. U.S. Pat. No. 5,030,786 (Shamshoum) and U.S. Pat. No. 5,980,859 (Gajda), and European patent 0,467,007 (Butler), which are incorporated herein by reference, describe the production of alkyl aromatic compounds with zeolite Beta, zeolite Y, and zeolite Omega U.S. Pat. No. 5,522,984 (Gajda), U.S. Pat. No. 5,672,799 (Perego), U.S. Pat. No. 5,980,859 (Gajda), and U.S. Pat. No. 6,162,416 (Gajda), which are incorporated herein by reference, teach the production of cumene with zeolite beta. Use of zeolite Mordenite in production of monoalkylated benzene such as cumene and ethylbenzene is described in U.S. Pat. No. 5, 198,595 (Lee), which is incorporated herein by reference. Production of ethylbenzene with ex situ selectivated zeolite catalyst is described in U.S. Pat. No. 5,689,025 (Abichandani), which is incorporated herein by reference. Production of ethylbenzene with ZSM-5 is described in U.S. Pat. No. 5,157,185 (Chu), which is incorporated herein by reference.

Production of ethylbenzene over intermediate pore size zeolites is described in U.S. Pat. No. 3,751,504 (Keown), U.S. Pat. No. 4,547,605 (Kresge), and U.S. Pat. No. 4,016,218 (Haag), which are incorporated herein by reference. U.S. Pat. No. 4,169,111 (Wight) and U.S. Pat. No. 4,459,426 (Inwood), which are incorporated herein by reference, disclose production of ethylbenzene over large pore size zeolites such as zeolite Y. Synthesis of zeolite ZSM-12 is described in U.S. Pat. No. 5,021,141 (Rubin), which is incorporated herein by reference. A process for ethylbenzene production over zeolite ZSM-12 is described in U.S. Pat. No. 5,907,073 (Kumar), which is incorporated herein by reference. Production of ethylbenzene over zeolite Mordenite is described in U.S. Pat. No. 5,430,211 (Pogue), which is incorporated herein by reference. Liquid phase synthesis of ethylbenzene with zeolite Beta is described in U.S. Pat. No. 4,891,458 (Innes) and U.S. Pat. No. 6,060,632 (Takamatsu), which are incorporated herein by reference. U.S. Pat. No. 4,849,569 (Smith), U.S. Pat. No. 4,950,834 (Arganbright), U.S. Pat. No. 5,086,193 (Sy), U.S. Pat. No. 5,113,031 (Sy), and U.S. Pat. No. 5,215,725 (Sy), which are incorporated herein by reference, teach various systems for the catalytic distillation production of alkylated aromatic compounds, including ethylbenzene and cumene.

The term "aromatic" in reference to the alkylatable compounds which are useful herein is to be understood in accordance with its art-recognized scope which includes alkyl substituted and unsubstituted mono-and polynuclear compounds. Compounds of an aromatic character which possess a heteroatom (e.g., N or S) are also useful provided they do not act as catalyst poisons under the reaction conditions selected. Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction. Suitable aromatic hydrocarbons include benzene, naphthalene, anthracene, naphthacene, perylene, coronene, and phenanthrene.

Generally the alkyl groups which can be present as substituents on the aromatic compound contain from 1 to about 22 carbon atoms and preferably from about 1 to 8 carbon atoms, and most preferably from about 1 to 4 carbon atoms. Suitable alkyl substituted aromatic compounds include toluene; xylene; isopropylbenzene; normal propylbenzene; alpha-methylnaphthalene; ethylbenzene; cumene; mesitylene; durene; p-cymene; butylbenzene; pseudocumene; o-diethylbenzene; m-diethylbenzene; p-diethylbenzene; isoamylbenzene; isohexylbenzene; pentaethylbenzene; pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. Reformate, especially reformate containing substantial quantities of benzene, toluene, and/or xylene, would also constitute a useful feed for the alkylation process of this invention.

The alkylating agents which are useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins can also be useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Typical aromatic alkylation reactions which may be improved by the present invention include obtaining ethylbenzene from the reaction of benzene with ethylene, cumene from the reaction of benzene with propylene, ethyltoluene from the reaction of toluene with ethylene, and cymenes from the reaction of toluene with propylene. The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0° C. to about 500° C., and preferably between about 50° C. and about 250° C.; a pressure of from about 0.2 to about 250 atmospheres; and preferably from about 5 to about 100 atmospheres, a molar ratio of alkylatable aromatic compound to alkylating agent of from about 0.1:1 to about 50:1, and preferably can be from about 0.5:1 to about 10:1; and a feed weight hourly space velocity (WHSV) of between about 0.1 and 500 $hr^{-1}$, preferably between 0.5 and 100 $hr^{-1}$.

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen. When benzene is alkylated with ethylene to produce ethylbenzene, the alkylation reaction may be carried out in the liquid phase. Suitable liquid phase conditions include a temperature between 150° C. and 316° C., preferably between 205° C. and 260° C.; a pressure up to about 3000 psig (20875 kPa); preferably between 400 and 800 psig (2860 and 5600 kPa), a space velocity between about 0.1 $h^{-1}$ and 20 $h^{-1}$ WHSV, preferably between 1 and 6 $h^{-1}$ WHSV, based on the ethylene feed; and a ratio of the benzene to the ethylene in the alkylation reactor from 1:1 to 30:1 molar, preferably from about 1:1 to 10:1 molar.

As regards the dry colorimetry analysis the principle has been explained above. A sample of the feedstock to be analyzed is vaporized, unless it is available under gasous phase, and is sent through a porous substrate carrying a reagent which changes color in proportion with the impurities. The liquid sample, if any, can be vaporized by any means. The porous substrate can be paper like filter paper. The porous substrate carries a chemical reagent specific to the nitrogen containing compounds impurities and advantageously responds to ammonia ($NH_3$ or $NH_4OH$), methylamine, dimethylamine, ethylamine and trimethylamine. This chemical reagent also reacts positively to $H_2S$ but normaly $H_2S$ is not present in the aromatic substrate feed and in the alkylating agent feed. The color is compared with standart colors obtained with samples containing known amounts of nitrogen containing compounds (the calibration). Any means can be used for the comparison. Advantageously an electronic device such as a photo optical system reads the color and by comparison with the standart colors converts the color to the amount of impurities. Advantageously the range is 30 wppb-25 wppm. The gas sample to be analyzed flows through the porous substrate carrying the reagent during about 1 to 5 minutes in accordance with the calibration.

To improve the response in time, many such apparatus can be used in parallel and a measurement is launched e.g. every minute or every ten seconds. Should the impurities are found to be higher than a requested level the reactor containing the catalyst can be temporarily by-passed. By way of example the above analysis can be made by an automatic device supplied by C.I. Analytics in Canada under the reference Sensi-tape® 7510.

During operation, the Sensi-Tape® is incremented through a sampling "window" where it is exposed to a metered sample stream. If the target gas is present, a stain proportional to the concentration develops. Simultaneously, a beam of light is reflected off the exposed portion of the tape and the intensity is measured continuously. As the amount of reflected light decreases due to stain development, the reduction is sensed by a photocell detector as an analog signal. This signal is converted to a digital format, matched to the gas response curve stored in the analyzer's permanent memory, and displayed/documented as the actual concentration value. All of these functions are microprocessor controlled. The use of this spectrophotometric technique, in combination with microprocessor control, provides excellent accuracy, repeatability, and detectability of low ppb (parts-per-billion) concentrations.

The invention claimed is:
1. A process for the alkylation of an aromatic substrate comprising:
   providing an alkylation reaction zone containing an alkylation catalyst;
   introducing a feedstock comprising an aromatic substrate, an alkylating agent, and an amount of nitrogen containing compounds selected from a group consisting of methylamine, dimethylamine, ethylamine, trimethylamine, or combinations thereof into an inlet of the alkylation reaction zone and into contact with the alkylation catalyst;
   operating the alkylation reaction zone at temperature and pressure conditions sufficient to cause alkylation of the aromatic substrate in the presence of the alkylation catalyst to produce an alkylation product comprising a mixture of the aromatic substrate, monoalkylated aromatic components, and polyalkylated aromatic components;
   withdrawing the alkylation product from the alkylation reaction zone, wherein amounts of the nitrogen containing compounds in the feedstock are monitored in a range of from 15 to 35 wppm by dry colorimetry, wherein the monitoring of the amounts of the nitrogen containing compounds comprises:
      vaporizing a sample of the feedstock, or obtaining a sample of the feedstock that is in the gaseous phase; and
      sending the sample through a porous substrate carrying a reagent that changes color in proportion with the amount of the nitrogen containing compounds.

2. The process of claim 1, wherein the aromatic substrate is benzene and the alkylating agent is propylene.

3. The process of claim 1, wherein the aromatic substrate is toluene and the alkylating agent is ethylene.

4. The process of claim 1, wherein the aromatic substrate is toluene and the alkylating agent is propylene.

5. The process of claim 1, wherein the aromatic substrate is an unsubstituted aromatic substrate.

6. The process of claim 1, wherein the aromatic substrate is a substituted aromatic substrate.

7. The process of claim 1, wherein the aromatic substrate is benzene, toluene, xylene, naphthalene, anthracene, naphthacene, perylene, coronene or phenanthrene.

8. The process of claim 1, wherein the aromatic substrate is selected from a group consisting of: toluene; xylene; isopropylbenzene; normal propylbenzene; alpha-methylnaphthalene; ethylbenzene; cumene; mesitylene; durene; p-cymene; butylbenzene; pseudocumene; o-diethylbenzene; m-diethylbenzene; p-diethylbenzene; isoamylbenzene; isohexylbenzene; pentaethylbenzene; pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene.

9. The process of claim 1, wherein the aromatic substrate is selected from a group consisting of hexylbenzene, nonylbenzene, dodecylbenzene, pentadecylbenzene, hexyltoluene, nonyltoluene, dodecyltoluene, and pentadecytoluene.

10. The process of claim 1, wherein the alkylating agent has 1 to 5 carbon atoms.

11. The process of claim 1, wherein the alkylating agent is an olefin.

12. The process of claim 11, wherein the olefin is ethylene, propylene, butene, or pentene.

13. The process of claim 1, wherein the alkylating agent is an alcohol.

14. The process of claim 13, wherein the alcohol is methanol, ethanol, propanol, butanol, or pentanol.

15. The process of claim 1, wherein the alkylating agent is an aldehyde.

16. The process of claim 15, wherein the aldehyde is formaldehyde, acetaldehyde, propionaldehyde, butraldehyde, or n-valeraldehyde.

17. The process of claim 1, wherein the alkylating agent is an alkyl halide.

18. The process of claim 17, wherein the alkyl halide is methyl chloride, ethyl chloride, propyl chloride, butyl chloride, or pentyl chloride.

19. The process of claim 1, wherein the amounts of nitrogen containing compounds are monitored in a range of from 25 to 30 wppm.

20. The process of claim 1, wherein the alkylation reaction zone is operated in the liquid phase.

* * * * *